(12) United States Patent
Ma

(10) Patent No.: US 8,367,059 B2
(45) Date of Patent: Feb. 5, 2013

(54) MATERIALS AND METHODS FOR CRYOPRESERVED BONE CONSTRUCTS

(75) Inventor: Teng Ma, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 13/184,357

(22) Filed: Jul. 15, 2011

(65) Prior Publication Data

US 2012/0020934 A1 Jan. 26, 2012

Related U.S. Application Data

(60) Provisional application No. 61/364,637, filed on Jul. 15, 2010.

(51) Int. Cl.
*A01N 63/00* (2006.01)
*C12N 11/02* (2006.01)
*C12N 5/00* (2006.01)

(52) U.S. Cl. .................. 424/93.7; 435/177; 435/325

(58) Field of Classification Search .............. 424/93.7; 435/177, 325
See application file for complete search history.

(56) References Cited

U.S. PATENT DOCUMENTS 5,763,267 A * 6/1998 Kurjan et al. ............ 435/293.1
2011/0229970 A1 * 9/2011 Ma ................................ 435/455

OTHER PUBLICATIONS

Zhao et al. Preparation and histological evaluation of biomimetic three-dimensional hydroxyapatite/chitosan-gelatin network composite scaffolds. Biomaterials 23 (2002) 3227-3243.*
Amaral, IF. et al. Rat bone marrow stromal cell osteogenic differentiation and fibronectin adsorption on chitosan membranes: The effect of the degree of acetylation. *Journal of Biomedical Materials Research Part A*, 75, 387-397, 2005.
Bensamoun, SF, Hawse, JR and Subramaniam, M. et al. TGF-beta inducible early gene-1 knockout mice display defects in bone strength and microarchitecture. *Bone*, 39, 1244-1251, 2006.
Boyce T, Edwards J, Scarborough N. Allograft bone: The influence of processing on safety and performance. *Orthop Clin North Am*, 30, 571-581, 1999.
Caplan, AI. Adult mesenchymal stem cells for tissue engineering versus regenerative medicine. *J of Cellular Physiology*, 213, 341-347, 2007.
Caplan, AI. Mesenchymal stem cell: cell-based reconstructive therapy in orthopaedics. *Tiss. Eng.*, 11, 1198-1211, 2005.
Caplan, AI. Why are MSCs therapeutic? New data: new insight. *Journal of Pathology*, 217, 318-324, 2009.
De Rosa, A. et al. A new method for cryopreserving adipose-derived stem cells: An attractive and suitable large-scale and long-term cell banking technology. *Tissue Eng Part C*, 15, 659-667, 2009.
Grayson, WL, MA, T and Bunnell, B. Human Mesenchymal Stem Cells Tissue Development in 3D PET Matrices. *Biotechnology Progress*, 20, 905-912, 2004.
Grayson, WL, Zhao, F, Bunnell, B and MA, T. Hypoxia enhances proliferation and tissue formation of human mesenchymal stem cells. *Biochemical and Biophysical Research Communications*, 358, 948-953, 2007.
Grayson, WL, Zhao, F, Izadpanah, R, Bunnell, B, MA, T. Effects of hypoxia on human mesenchymal stem cell expansion and plasticity in 3D constructs. *Journal of Cellular Physiology*, 207, 331-339, 2006.
Gullihorn, L, Karpman, R and Lippiello, L. Differential effects of nicotine and smoke condensate on bone cell metabolic activity. *Orthop Trauma*, 19, 17-22, 2005.
Horwitz EM, Gordon PL, Koo WK. et al. Isolated allogeneic bone marrow-derived mesenchymal cells engraft and stimulate growth in children with osteogenesis imperfecta: implications for cell therapy of bone. *Proc Natl Acad Sci USA*, 99, 8932-8937, 2002.
Horwitz EM, Prockop DJ, Fitzpatrick LA. et al. Transplantability and therapeutic effects of bone marrow-derived mesenchymal cells in children with osteogenesis imperfecta. *Nat. Med.*, 5, 309-313, 1999.
Hosseinkhani, H, Yamamoto, M and Inatsugu, Y. Enhanced ectopic bone formation using a combination of plasmid DNA impregnation into 3D scaffold and bioreactor perfusion system. *Biomaterials*, 27, 1387-1398, 2006.
Johnston, P, Gurusamy, KS and Parker, MJ. Smoking and hip fracture; a study of 3617 cases. *Injury*, 37, 152-156, 2006.
Kadiyala, S. et al. Culture expanded canine mesenchymal stem cells possess osteochondrogenic potential in vivo and in vitro. *Cell Transplantation*, 6, 125-134, 1997, abstract only.
Kern, S. et al. Comparative Analysis of Mesenchymal Stem Cells from Bone Marrow, Umbilical Cord Blood, or Adipose Tissue. *Stem Cells*, 24, 1294-1301, 2006.
Kilpadi, KL, Chang, PL, and Bellis, SL. Hydroxylapatite binds more serum proteins, purified integrins, and osteoblast precursor cells than titanium or steel. *J Biomed Mater Res*, 57, 258-267, 2001.
Kim, HW, Kim, HE and Salih, B. Stimulation of osteoblast responses to biomimetic nanocomposites of gelatin—hydroxyapatite for tissue engineering scaffolds. *Biomaterials*, 26, 5221-5230, 2005.
Kon, E, Muraglia, A. et al. Autologous bone marrow stromal cells loaded onto porous hydroxyapatite ceramic accelerate bone repair in critical size defects of sheep long bones. *J. Biomed. Mater Res*, 49, 328-337, 2000.
Krebsbach, PH, Mankani, MH and Satomura, K. Repair of craniotomy defects using bone marrow stormal cells. *Transplantation*, 66, 1272-1278, 1998.

(Continued)

*Primary Examiner* — Karen Cochrane Carlson
*Assistant Examiner* — Natalie Moss
(74) *Attorney, Agent, or Firm* — Saliwanchik, Lloyd & Eisenschenk; Doran R. Pace

(57) ABSTRACT

Porous HCG scaffolds are provided in a perfusion bioreactor. Cells are seeded in the HCG scaffolds and cell culture media is perfused through the bioreactor to allow for cell seeding and growth. The cell culture media is removed, the HCG-cell constructs washed, and then preserved in the bioreactor with a perfusion comprising cryopreservation fluid comprising one or more of DMSO, trehalose, glycerol, ethylene glycol, or serum. The HCG-cell constructs (or the perfusion chambers containing them) are then removed from the bioreactor and placed in a cryopreservant media and maintained at about −80° C. The frozen HCG-cell constructs (or the chambers containing them) can then be stored at a suitable cryogenic temperature until needed. When needed, frozen HCG-cell constructs can be removed from cold storage and thawed using suitable means.

17 Claims, 4 Drawing Sheets

OTHER PUBLICATIONS

Kyrö A, Usenius JP, Aarnio M, Kunnamo I, Avikainen V. Are smokers a risk group for delayed healing of tibial shaft fractures? *Ann Chir Gynaecol*, 82, 254-262, 1993, abstract only.

Le Blanc K, Tammik C. et al. HLA expression and immunologic properties of differentiated and undifferentiated mesenchymal stem cells. *Exp Hematol*, 31, 890-896, 2003.

Le Blanc, K., Tammik, L., Sundberg, B., Haynesworth, S. E., and Ringden, O. Mesenchymal stem cells inhibit and stimulate mixed lymphocyte cultures and mitogenic responses independently of the major histocompatibility complex. *Scand. J. Immunol.*, 57, 11-20, 2003.

Li, Y, MA, T. et al. Effects of Filtration Seeding on Cell Density, Spatial Distribution, and Proliferation in Nonwoven Fibrous Matrices. *Biotech Progress*, 17, 935-944, 2001.

Lin, LW, Chow, KL, and Leng, Y. Study of hydroxyapatite osteoinductivity with an osteogenic differentiation of mesenchymal stem cells. *J Biomed Mater Res*, 89A, 326-335, 2009.

Logeart-Avramoglou, D, Anagnostou, F; Bizios, R; Petite, H. Engineering bone: challenges and obstacles. *J. Cell. Mol. Med.*, 9, 72-84. 2005, abstract only.

Mackenzie, EJ, Bosse, MJ, Kellam, JE. et al. Characterization of patients with high-energy lower extremity trauma. *J. Orthop Trauma*, 14, 455-66, 2000.

Martin, I. et al. Fibroblast growth factor-2 supports ex vivo expansion and maintenance of osteogenic precursors from human bone marrow. *Endocrinology*, 138, 4456-62, 1997.

Mauney, JR, Jaquiery, C. et al. In vitro and in vivo evaluation of differentially demineralized cancellous bone scaffolds combined with human bone marrow stromal cells for tissue engineering. *Biomaterials*, 26, 3173-3185, 2005.

Moghaddam, A. et al. Cigarette smoking decreases TGF-b1 serum concentrations after long bone fracture. *Injury, Int. J. Care Injured*, 41, 1020-1025, 2010.

O'Brien, FJ. et al. The effect of pore size on cell adhesion in collagen-GAG scaffolds. *Biomaterials*, 26, 433-441, 2005.

Olofsson, H, Byberg, L and Mohsen R. et al. Smoking and the risk of fracture in older men. *Journal of Bone and Mineral Research*, 20, 1208-1215, 2005.

Perlman MH, Thordarson DB. Ankle fusion in a high risk population: an assessment of nonunion risk factors. *Foot Ankle Int*, 20, 491-496, 1999, abstract only.

Peter, M, Ganesh, N. et al. Preparation and characterization of chitosan—gelatin/nanohydroxyapatite composite scaffolds for tissue engineering applications. *Carbohydrate Polymers*, 80, 687-694, 2010.

Petite et al. Tissue-engineered bone regeneration. *Nat. Biotechnol.*, 18, 959-963, 2000.

Porter, SE and Hanley, EN. The Musculoskeletal Effects of Smoking. *J. Am. Acad Orthop Surg*, 9, 9-17, 2001.

Potier E. et al. Hypoxia affects mesenchymal stromal cell osteogenic differentiation and angiogenic factor expression. *Bone*, 40, 1078-1087, 2007.

Raikin SM, Landsman JC, Alexander VA, Froimson MI, Plaxton NA. Effect of nicotine on the rate and strength of long bone fracture healing. *Clin Orthop*, 353, 231-237, 1998, abstract only.

Schaeren, S, Jaquiery, C. et al. Effect of bone sialoprotein coating of ceramic and synthetic polymer materials on in vitro osteogenic cell differentiation and in vivo bone formation. *J Biomed Mater Res A*, 92, 1461-1467, 2010.

Shang, Q. et al. Tissue-engineered bone repair of sheep cranial defects with autologous bone marrow stromal cells. *J. Craniofac Surg*, 12, 586-593, 2001.

Sionkowska, A. et al. Molecular interactions in collagen and chitosan blends. *Biomaterials*, 25, 795-801, 2004.

Skott, M. et al. Tobacco extract but not nicotine impairs the mechanical strength of fracture healing in rats. *J Orthop Res*, 24, 1472-1479, 2006.

Tosounidisa, T. et al. Fracture healing and bone repair: an update. *Trauma*, 145-156, 2009.

Utting, JC. et al. Hypoxia inhibits the growth, differentiation and bone-forming capacity of rat osteoblasts. *Experimental Cell Research*, 312, 1693-1702, 2006.

Whyte MP, Kurtzberg J, McAlister WH. et al. Marrow cell transplantation for infantile hypophosphatasia. *J Bone Miner Res*, 18, 624-636, 2003.

Wipfli, H and Samet, JM. Global Economic and Health Benefits of Tobacco Control: Part 1. *Clin Pharmacol Ther*, vol. 86, 263-271, 2009.

Wipfli, H and Samet, JM. Global Economic and Health Benefits of Tobacco Control: Part 2. *Clin Pharmacol Ther*, vol. 86, 272-280, 2009.

Woods, EJ. et al. Optimized cryopreservation method for human dental pulp-derived stem cells and their tissues of origin for banking and clinical use. *Cryobiology*, 59, 150-157, 2009.

Xu, JZ, Hui, Q. et al. Repair of large segmental bone defects using bone marrow stromal cells with demineralized bone matrix. *Orthopaedic Surgery*, 1, 34-41, 2009.

Zhao, F and Ma, T. Perfusion bioreactor system for human mesenchymal stem cell tissue engineering: Dynamic cell seeding and construct development. *Biotechnology and Bioengineering*, 91, 482-493, 2005.

Zhao, F, Chella, R and Ma, T. Effects of Shear Stress on 3-D Human Mesenchymal Stem Cell Construct Development in a Perfusion Bioreactor System: Experiments and Hydrodynamic Modeling. *Biotechnology and Bioengineering*, 96, 584-595, 2007.

Zhao, F, Grayson, WL and Ma, T. Perfusion Bioreactor Affects the Nuclear Shape and ECM Structure of Human Mesenchymal Stem Cells in 3D Scaffolds. *Journal of Cellular Physiology*, 219, 421-429, 2009.

Zhao, F, Grayson, WL, Ma, T, Bunnell, B, and Lu, WW. Effects of hydroxyapatite in 3-D chitosan—gelatin polymer network on human mesenchymal stem cell construct development. *Biomaterials*, 27, 1859-1867, 2006.

\* cited by examiner

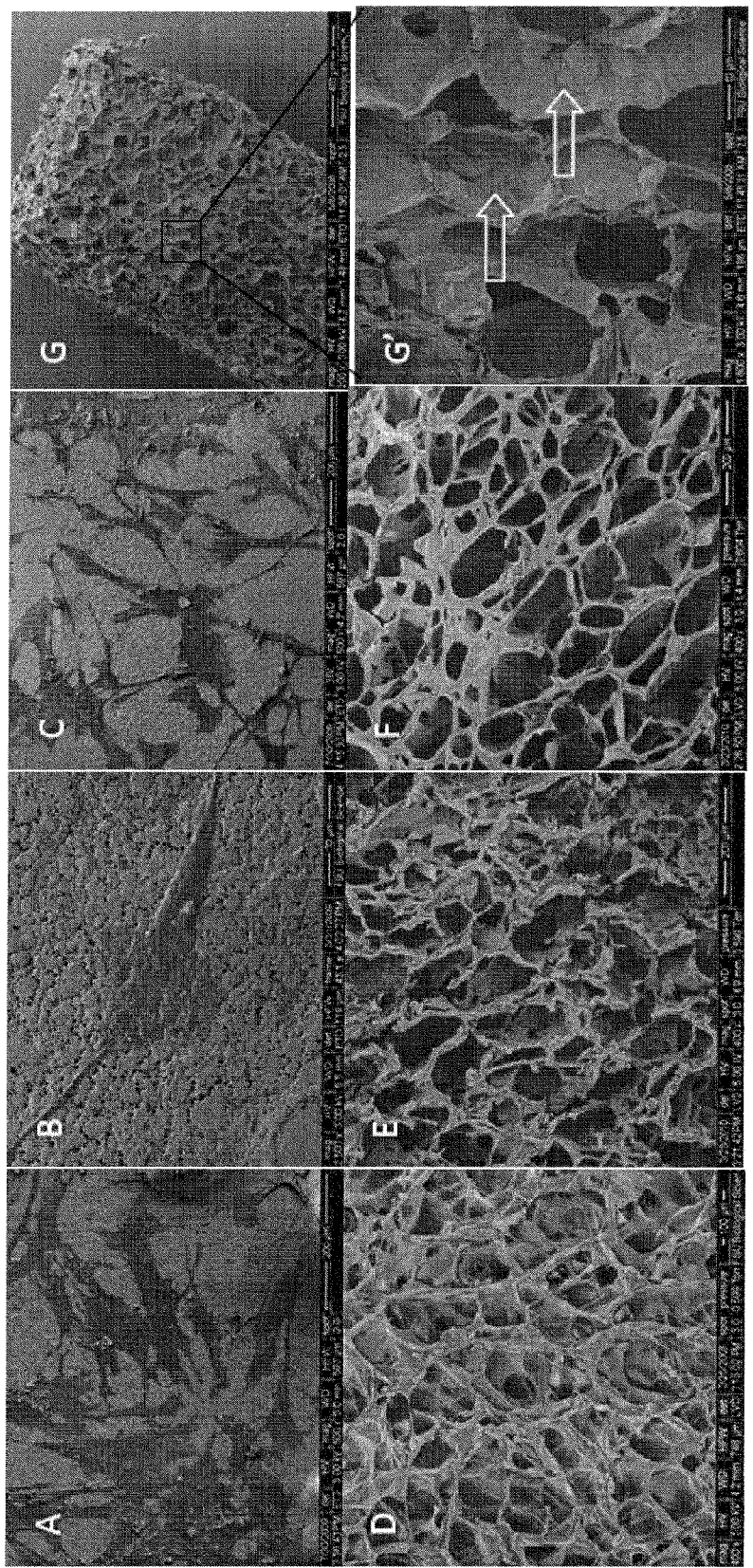

MATERIALS AND METHODS FOR CRYOPRESERVED BONE CONSTRUCTS

CROSS-REFERENCE TO RELATED APPLICATION

The present application claims the benefit of U.S. Provisional Application Ser. No. 61/364,637, filed Jul. 15, 2010, which is hereby incorporated by reference herein in its entirety, including any figures, tables, nucleic acid sequences, amino acid sequences, or drawings.

GOVERNMENT SUPPORT

This invention was made with government support under grant number W81 XWH-07-0363 awarded by the Department of Defense Peer Reviewed Medical Research Program. The government has certain rights in the invention.

BACKGROUND OF THE INVENTION

Bone fractures and defects are common in the general population, and management of fractures is the leading cause of all trauma admission for adolescents and adults under 65 years, generating $1.2 billion in hospital costs (1). While fracture healing is efficient and typically results in newly formed bone, a number of adverse conditions impair the healing process, leading to delayed healing and nonunion in a small but significant number of patients. Orthopedic surgeons have known for years that smoking is a major contributor to a variety of bone conditions including osteoporosis, lumbar disc disease, healing of fractures, the rate of hip fractures and bone cancer (2). Recent studies have started revealing the pathological mechanisms of smoking on musculoskeletal injuries and established a real and reproducible relationship between smoking and musculoskeletal diseases (2, 3). In particular, clinical studies have found that smokers have a significant longer time to clinical union, and a higher incidence of delayed union compared with non-smokers (4, 5). Addressing the needs and providing optimal care for these patients have important social and economical impact.

Artificial bone grafts regenerated by donor cells and biomaterials, also known as tissue engineered bone constructs (TEBC), represent a novel approach that overcomes the donor limitation and increases the efficacy for defect repair and healing. TEBC requires both an osteogenic cell source and a substrate material that can support the regeneration of healthy bone. Human mesenchymal stem cells (hMSCs), which are known to be responsible for the normal turnover and maintenance of adult mesenchymal tissues in vivo, are inducible osteoprogenitor cells and have become cell of choice in bone tissue regeneration (6, 7). On the other hand, natural and synthetic scaffolds seeded with culture expanded hMSCs have been extensively studied in bone tissue repair and regeneration and shown promising clinical results (8, 9, 10). The combination of hMSC with bioactive scaffolds has become an attractive approach to enhance bone healing for the patients such as smokers and elder patients who have impaired regeneration capacity and not responsive to conventional therapeutic intervention.

The treatment of fractures in young patients and osteoporotic fractures in elderly patients is a major part of trauma care. For young adults, critical size defect and delayed union are the major problem related to morbidity during healing, whereas osteoporosis-related complications are the major problem to the ageing population. Although the risks of tobacco smoking have been well known for decades, there are more than 50 million smokers in the U.S. and over 500,000 deaths can be attributed to smoking (2, 16). Cigarette smoking contributes to musculoskeletal diseases and influences an array of orthopaedic conditions from bone mineral density to the rate of hip fractures and fracture healing (2, 3). Smoking is known to reduce blood supply, has high levels of reactive oxygen intermediates, and low concentration of oxidant vitamins. Although nicotine at low doses may be stimulatory, high dose nicotine is directly toxic to proliferating osteoblasts (17). Nicotine has been shown to inhibit the strength of repair in a fracture model and in distraction osteogenesis in rabbit (18, 19). In addition to nicotine, other components of cigarette smoke may also be harmful. In animal study, tobacco extract not containing nicotine significantly reduced the mechanical strength of healing femoral fractures in rats (20). Clinical studies have found that smokers have a significant longer time to clinical union, and a higher incidence of delayed union compared with non-smokers (4). Smokers also have a higher rate of nonunion and poorer results after fusion of the ankle and spine (21). Smoking also induces osteoporosis and leads to increased risk of fracture in elderly men (22, 23). Together, these results suggest that cigarette smoking, whether it is the nicotine or other components of cigarettes, is a significant contributing factor in bone diseases and fracture healing.

The pathological mechanism that results in the adverse effects of cigarette smoking on bone disease and healing has begun to be revealed. Smoking influences the biochemical interactions and cellular properties that occur during fracture healing which leads to an impaired healing. For example, TGF-$\beta$1 is essential for bone formation and osteogenic differentiation, and TGF-$\beta$1 knockout mice have defect in bone strength and structure (24). In a recent study, TGF-$\beta$1 serum concentrations, which are considered to be one of the most important markers of fracture healing, are reduced by smoking, and the reduction of TGF-$\beta$1 serum concentration in smokers is statistically significant during the 4th week after surgery (25). In addition to the molecular milieu, smoking also affects cellular properties that are crucial mediators of wound repair and healing. Mesenchymal stem cells (MSCs) regulate the normal bone homeostasis and are inducible osteoblast progenitors (6). MSCs are also significant source of cytokines that mediate inflammatory response and participate in wound healing. Smoking compromises hMSC's ability for cytokine secretion and down-regulate their osteoblastic differentiation due to reduced blood supply and high concentration of free radicals and toxins associated with smoking, inhibiting patient's self-healing process (26, 27). Implantation of constructs containing hMSCs from healthy donor could augment self-healing capacity and improve clinical outcome.

Promotion of bone healing through biological means is a major therapeutic option for trauma surgeons. Bone graft is the second most commonly transplanted tissue following blood (28). While numerous types of grafts have been used, the ideal bone graft should be an optimal combination of osteogenic, osteoinductive, and osteoconductive properties. These porous implantable materials not only act as a 3D template for bone growth but their degradation products also have no toxic effects. To further enhance the bone regeneration potential, these bioresorbable scaffolds are often impregnated with suitable cell types that augment bone regeneration process. In this effort, it is advantageous to select a scaffolding material to mimic natural tissue composition in addition to promoting hMSC proliferation and differentiation. Chitosan, gelatin, and hydroxyapatite in various combinations are among frequently studied biomimetic composite scaffolds for bone regeneration because of their chemical similarity to natural extracellular matrix (ECM) (11, 29, 30, 31). Chitosan, a linear polysaccharide is composed of glucosamine and N-acetyl glucosamine units linked by β(1-4) glycosidic bonds. Structural similarity of chitosan with various glycosaminoglycans (GAGs) found in the extracellular matrix of bone and cartilage has made chitosan an attractive material in bone and cartilage tissue regeneration. The cationic nature of chitosan allows for mimicking the ECM-rich environment of bone tissue through the formation of insoluble ionic complexes with anionic molecules such as growth factors, glycosaminoglycans (GAG), and proteoglycans benefiting cell growth and tissue formation (32). Gelatin is a partially denaturalized collagen and retains moieties that facilitate cell adhesion and influence cell behaviors (33). The abundance of functional groups in gelatin allows for interaction with growth factors and forms a favorable microenvironment for tissue regeneration. Hydroxyapatite (HA) is the mineral component of natural bone ECM and has been used to improve biocompatibility and hard tissue integration through the sequestering of serum proteins (34). Our laboratory has developed a composite of hydroxyapatite-chitosan-gelatin and demonstrated that the presence of HA improves protein adsorption in the porous HCG scaffolds and enhances hMSC long-term growth and osteogenic differentiation upon induction (11).

Recent advances in human mesenchymal stem cells (hMSC) provide a promising cell source that is readily available from adult donor, is easy to be expanded in culture, and has high potential to differentiate into bone tissue. Originally isolated from bone marrow, but now identified in multiple tissue sources, MSCs are multi-potent progenitor cells responsible for the repair and regeneration of mesenchymal tissue such as bone, cartilage, fat, and muscle (6, 35). Along with considerable in vitro studies, autologous bone marrow-derived MSCs have also been used in various bone diseases and demonstrated their therapeutic potential in patients (36, 37, 38, 39). MSC have been combined with 3-D biomaterials to repair the site-specific bone defect with good results (40, 41). In both large and small animal models, the implantation of MSC-seeded constructs has demonstrated their ability to accelerate the repair of femoral defects, craniomaxillofacial deformities, and spinal fusion (42, 43). In addition to their multipotentiality, MSCs have unique immunosuppressive properties which allow allogeneic transplantation without the need of immunosuppression (44, 45). This has significant implication in human therapy because MSCs derived from healthy donors can be cryopreserved and made available for patients in a variety of acute and chronic clinical settings. Studies have shown that MSCs can survive freezing temperatures without significant change in viability, indicating their potential for future "off-the-shelf" therapeutic applications (46). Despite the success in cryopreserving cells in suspension, methods for the cryopreservation of the constructs loaded with cells has not been reported. Although the "off-the-shelf" constructs are cost effective and provide the flexibility needed for the surgical room, cryopreservation of TEBCs remains a technical barrier and little is known about the impact of such procedure on cell viability and regeneration potency (15).

Our laboratory has developed a hydroxyapatite-chitosan-gelatin (HCG) scaffold and successfully demonstrated its superior properties for bone regeneration when infused with hMSCs (11, 12). We have also developed a perfusion bioreactor system that integrates cell seeding and long-term tissue growth, which significantly improving system efficiency and construct properties (13, 14). Using the perfusion bioreactor system developed in our lab, we have also shown that dynamic cell seeding into the center of the 3D HCG porous scaffolds and supports long-term construct growth, thereby streamlining the fabrication process (see preliminary results). The in vitro and animal studies have shown promising results for HCG's application in bone regeneration. HCG scaffolds and the perfusion bioreactor system establishes a technology platform required for the fabrication of functional bone constructs from hMSC.

BRIEF SUMMARY OF THE INVENTION

The subject invention concern materials and methods for cryopreservation of HCG-cell constructs. In one embodiment, porous HCG scaffolds are provided in a perfusion bioreactor having perfusion chambers that can contain the HCG scaffolds, cells are then seeded in the HCG scaffolds in the perfusion bioreactor, cell culture media is perfused through and the bioreactor operated so as to allow for cell seeding and growth in the HCG scaffold. After a suitable period of time, the cell culture media is removed and the HCG containing cells (HCG-cell constructs) can be washed with a suitable buffer, such as phosphate-buffered saline (PBS). The HCG-cell constructs are then perfused with a suitable cryopreservation fluid transversely across the HCG-cell constructs in the bioreactor. The cryopreservant can comprise one or more of the following: DMSO, trehalose, glycerol, ethylene glycol, and serum for cell culture (e.g., fetal bovine serum (FBS)). In one embodiment, the HCG-cell constructs are perfused for a suitable period of time with cryopreservant fluid using transverse flow of the fluid in the bioreactor at a suitable flow rate. The HCG-cell constructs (or the perfusion chambers containing them) are then removed from the bioreactor and placed in a cryopreservant media and maintained at increasingly colder temperatures until temperatures reach about $-80°$ C. The frozen HCG-cell constructs (or the chambers containing them) can then be stored at a suitable cryogenic temperature (e.g., in liquid nitrogen) until needed. When needed, frozen HCG-cell constructs can be removed from cold storage and thawed using suitable means (e.g., $37°$ C. water bath). Cells contemplated for use in the present invention include stem cells, such mesenchymal stem cells. Cells can be animal cells, such as mammalian cells. In one embodiment, the cells are human cells.

BRIEF DESCRIPTION OF THE DRAWINGS

FIGS. 3A-3G, 3G-1. hMSC have high affinity to the HCG gel (FIGS. 3A-3C). They spread on HCG surface after 24 hrs and are able to burrow into the gel (FIGS. 3B, 3C) after 7 days. The pore size of HCG sponges inversely correlated to freezing temperature (FIG. 3D: 160 μm at $-20°$ C.; FIG. 3E: 130 μm at $-50°$ C.; FIG. 3F: 100 μm at $-80°$ C.). HCG scaffolds maintain structural integrity after 30 days in the perfusion bioreactor (FIG. 3G), with extensive hMSC ingrowth in the center of the scaffolds (arrows) (FIG. 3G-1).

DETAILED DESCRIPTION OF THE INVENTION

Figure 1:
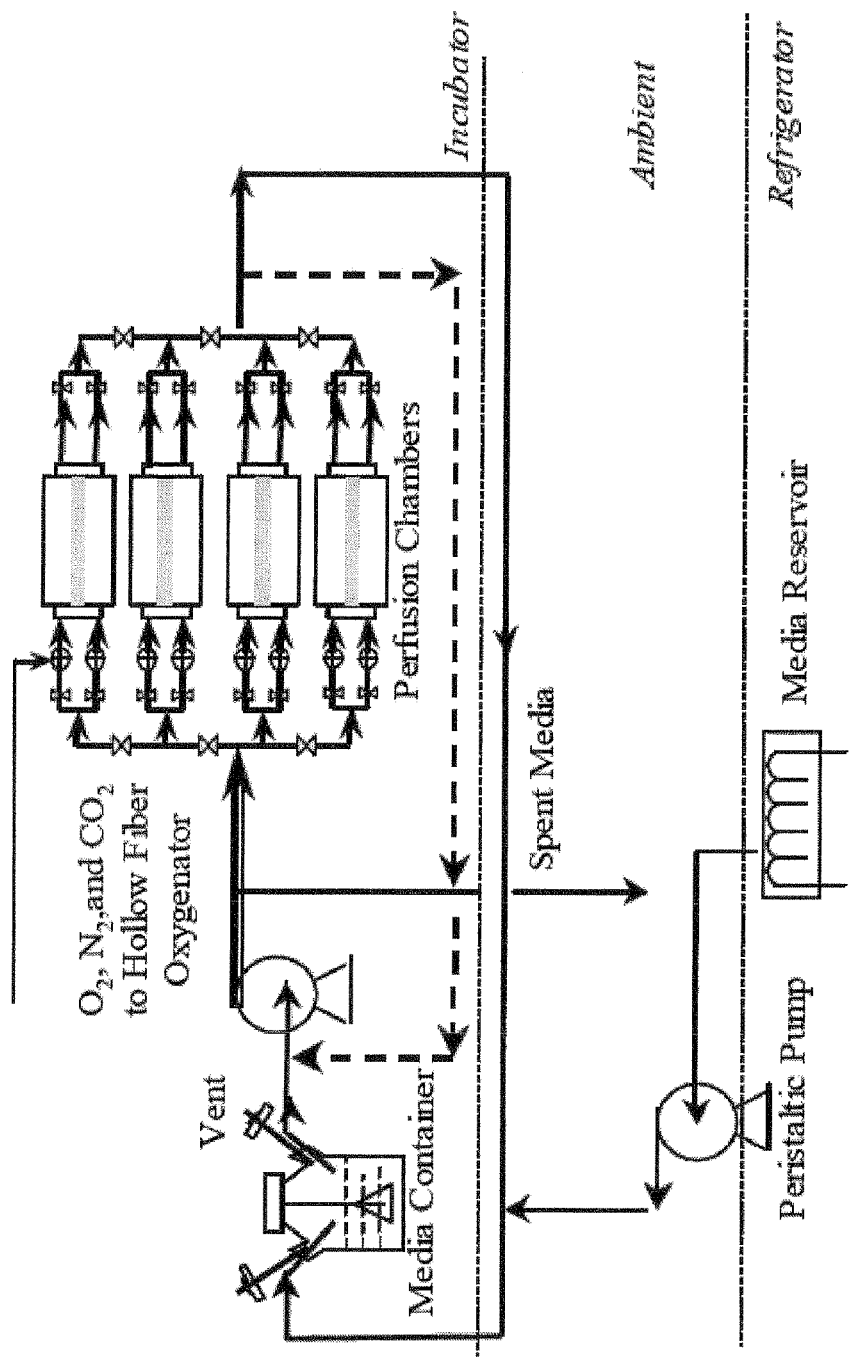
FIG. 1. The in-house perfusion bioreactor system comprises multiple chambers and has the capacity to modulate flow direction in each chamber, facilitating cell seeding and long-term cell growth. In this study, cryogen will be perfused through the 3D constructs to improve spatial distribution and better preserve cell viability.

The subject invention concerns cryopreservation methods for preserving the HCG-hMSC constructs. In order for the TEBCs to be cost effective and provide flexibility in a surgical setting, they will need to be manufactured as "off-the-shelf" materials that are pre-loaded with cells and cryopreserved. However, cryopreservation is a significant technical challenge and the effects of long-term storage are unknown for the HCG-hMSC constructs. In fact, maintaining and demonstrating the viability of TEBCs following cryopreservation and storage has been considered "the Achilles' heel" of this type of products and must be addressed to move the product to market (15).

The subject invention concern materials and methods for cryopreservation of HCG-cell constructs. In one embodiment, porous HCG scaffolds are provided in a perfusion bioreactor having perfusion chambers that can contain the HCG scaffolds, cells are then seeded in the HCG scaffolds in the perfusion bioreactor, cell culture media is perfused through and the bioreactor operated so as to allow for cell seeding and growth in the HCG scaffold. After a suitable period of time, the cell culture media is removed and the HCG containing cells (HCG-cell constructs) can be washed with a suitable buffer, such as phosphate-buffered saline (PBS). The HCG-cell constructs are then perfused in the bioreactor with a suitable cryopreservation fluid. The cryopreservant can comprise one or more of the following: DMSO, trehalose, glycerol, ethylene glycol, and serum for cell culture (e.g., fetal bovine serum (FBS)). In one embodiment, the HCG-cell constructs are perfused for a suitable period of time with cryopreservant fluid using transverse flow of the fluid in the bioreactor at a suitable flow rate. The HCG-cell constructs (or the perfusion chambers containing them) are then removed from the bioreactor and placed in a cryopreservant media and maintained at increasingly colder temperatures until temperatures reach about −80° C. The frozen HCG-cell constructs (or the chambers containing them) can then be stored at a suitable cryogenic temperature (e.g., in liquid nitrogen) until needed. When needed, frozen HCG-cell constructs can be removed from cold storage and thawed using suitable means (e.g., 37° C. water bath). Cells contemplated for use in the present invention include stem cells, such mesenchymal stem cells. Cells can be animal cells, such as mammalian cells. In one embodiment, the cells are human cells.

In one embodiment, a porous HCG scaffold used in the present methods is in the three-dimensional shape of a bone or tissue or a portion of a bone or tissue. For example, the HCG scaffold can be in the shape of a femur, a tibia, a fibula, a humerus, a radius, an ulna, a patella, a cranial bone, a maxillofacial bone, a spinal bone, a scapula, a clavicle, a carpal or metacarpal bone, a tarsal or metatarsal bone, or a pelvic bone, or any other bone in an animal body.

The subject invention also concerns a cell or cells that have been cryopreserved using the methods of the invention. The subject invention also concerns, HCG-cell constructs that are prepared using the methods of the invention. The constructs can be provided in various three-dimensional shapes and sizes. The constructs can be provided in shapes that are similar to or that fit in the injury site of the tissue or bone to be repaired or replaced. The HCG-cell constructs of the invention can be in a frozen or thawed state. The cells can be any animal cell. In one embodiment, the cells are stem cells, such as mesenchymal stem cells. The cells can be from any animal, including insects, fish, reptiles, amphibians, birds, or mammals. In one embodiment, the cells are human cells. In an exemplified embodiment, the cells are human stem cells (e.g., human mesenchymal stem cells).

The subject invention also concerns kits comprising one or more containers and cryopreserved cells or cryopreserved HCG-cell constructs that are prepared using the methods of the present invention. Kits can optionally comprise instructions or labeling that describes how to maintain, store, thaw, and/or use the cryopreserved cells and constructs. Kits can also optionally comprise media for storage, maintenance, thawing, and/or growth of the cryopreserved cells and constructs.

The subject invention also concerns methods for treating or repairing or strengthening or replacing injured or defective tissue or bone, wherein an animal in need of treatment is administered or provided with cryopreserved cells and/or HCG-cell constructs of the present invention. In one embodiment, the methods are used to treat or repair a bone fracture. In another embodiment, the methods are used to repair or replace a missing or defective bone or a portion of a bone. In specific embodiments, the methods can be used to repair or accelerate repair of a long bone (e.g., a femur) defect, or a craniomaxillofacial defect or deformity, or in spinal fusion.

Figures 2A, 2B:
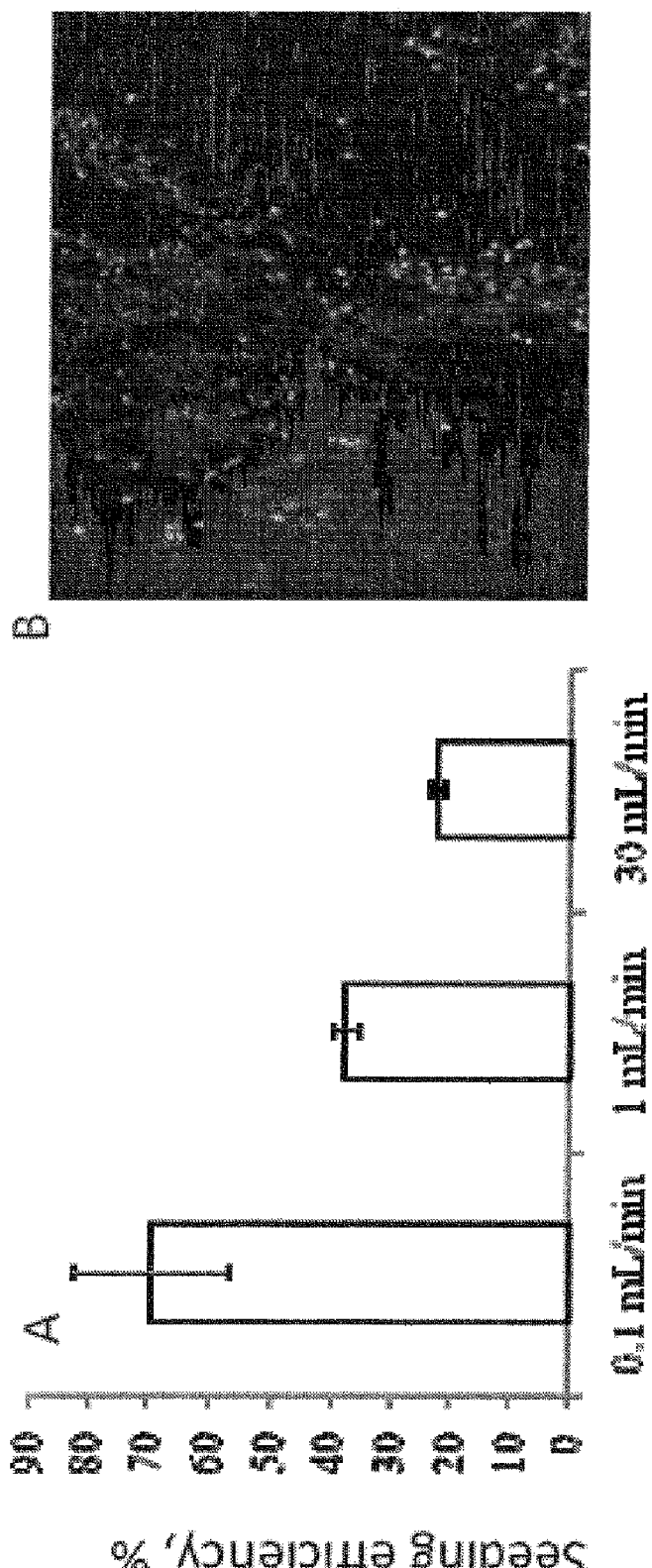
FIGS. 2A and 2B. Cell seeding efficiency decreases as flow rate increases (FIG. 2A). Dynamic cell seeding achieve better spatial distribution throughout the 3D HCG constructs as visualized by DAPI staining (FIG. 2B).
Figures 4A, 4B:
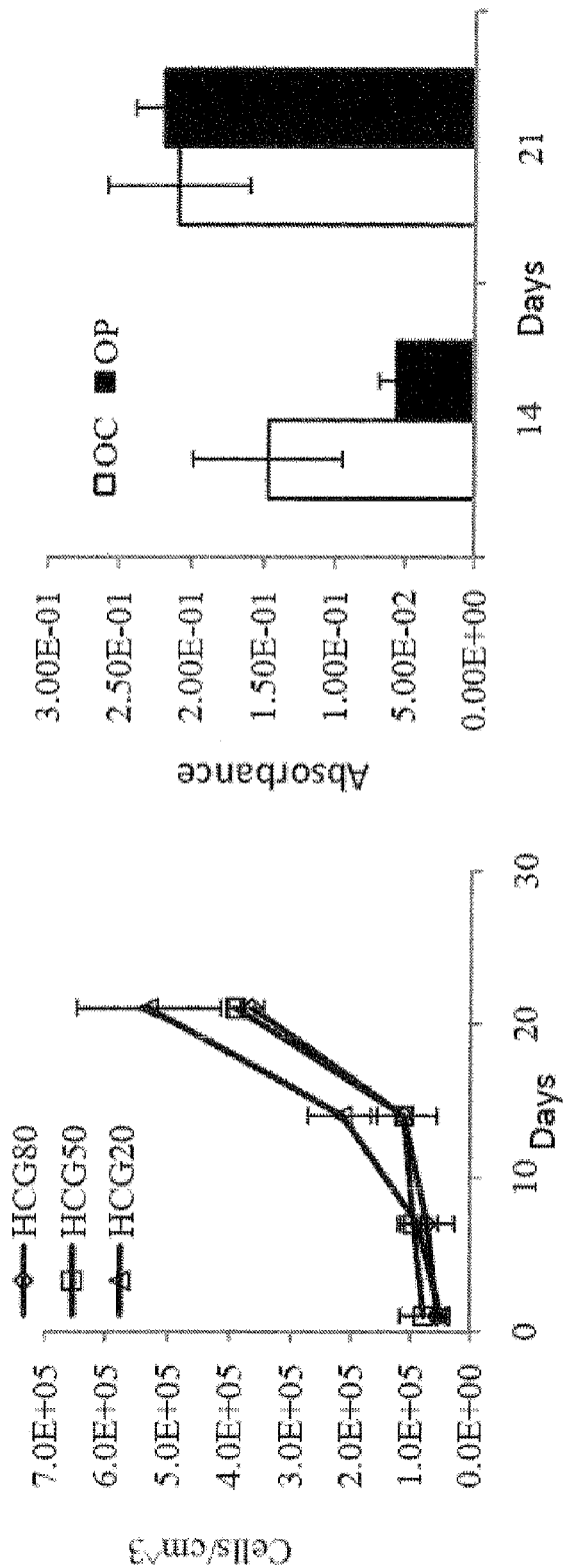
FIGS. 4A and 4B. hMSC have robust growth in the 3D HCG scaffolds but no difference observed for HCG with different pore sizes (FIG. 4A). Expressions of osteocalcin (OC) and osteopointin (OP) increased for the hMSC-HCG constructs over 3 weeks without chemical induction (FIG. 4B), indicating HCG's osteoinductive properties.

FIG. 1 shows the modular perfusion bioreactor system that allows modulation of flow mode, integrates cell seeding and long-term cultivation, and supports multiple constructs in a single system. Our laboratory has also developed the HCG biomimetic composite scaffold and investigated hMSC expansion and osteogenic differentiation in the 3-D HCG scaffolds (11). hMSC seeding efficiency is inversely correlated to flow rate while cell spatial distribution in the 3D HCG scaffolds can be significantly improved by perfusion seeding (FIG. 2). hMSCs have high affinity to the HCG scaffolds and are able to migrate into the HCG gel (FIGS. 3A-3C). The 3D HCG scaffolds with inter-connected pores can be readily fabricated by lyophilization, and the pore structure of the 3D HCG scaffolds can be controlled by freezing temperature (FIGS. 3D-3F). HCG scaffolds maintained their structural integrity after 3 weeks of culture in the perfusion bioreactor and hMSCs are able to penetrate into the interior of the scaffolds (FIGS. 3G and 3G-1), indicating perfusion enhances construct development. hMSC exhibited robust growth in the HCG scaffolds after perfusion seeding over a 3-week culture period (FIG. 4A). Expressions of osteocalcin (OC) and osteopointin (OP), two late stage bone markers, increased for the hMSC-HCG constructs over 3 weeks without chemical induction (B), indicating HCG's osteoinductive properties (FIG. 4B). Together, these results show that HCG scaffolds support hMSC growth and osteogenic differentiation and perfusion bioreactor system plays pivotal role in the fabrication of bone construct from hMSC in the HCG scaffolds.

We have developed a perfusion bioreactor-based cryopreservation method to disperse cryogen in the 3D TEBCs using the perfusion bioreactor system. The perfusion bioreactor-based cryopreservation method provides convective flow through the 3D TEBC, thereby improving spatial distribution of the cryopreservant fluids and reducing cell death. In addition, integrating cell seeding, construct cultivation, and cryopreservation in the perfusion bioreactor system also streamlines the process of construct fabrication and preservation and provides an automated system for the fabrication of multiple constructs.

Example 1

Development of Perfusion Cryopreservation Method

Although cryopreservants such as DMSO and trehalose have shown promising results in preserving adult stem cells in suspension, 3D engineered constructs have low permeability and greatly restrict fluid access to the interior of the constructs. Immersing the constructs in cryopreservant solution could result in uneven access to the cells, leading to cell death upon thawing. As a result, the conventional cryopreservation method cannot be extrapolated to the 3D constructs and technology that overcomes the transport barrier for effective cryopreservation of 3D TEBC is not yet available. The subject invention utilizes convective flow generated in the perfusion bioreactor to distribute the cryopreservant fluid transversely across the 3D constructs, thereby achieving uniform cell exposure to the cryopreservation solution. Convective flow in the perfusion bioreactor effectively overcomes the transport barriers in the 3D constructs and greatly reduces the toxic effects that compromises cell viability.

Experiments: Perfusion Bioreactor.

The modular, 3-D perfusion bioreactor system (see, for example, U.S. patent application Ser. No. 13/041,688 (filed Mar. 7, 2011)) that has been developed and utilized in our previous studies can be used. Four perfusion chambers in parallel with 3 chitosan scaffolds in each chamber can be utilized (FIG. 1). The system also includes a media container, two multi-channel peristaltic pumps, and a fresh media container stored in a refrigerator. The whole system, except for the pumps, can be placed in a 37° C. incubator to maintain a constant operating temperature. There are three circulating loops in the system: a main circulating loop, an inoculation loop, and a fresh media replenishing loop. The two inlets in each chamber are connected to independent inlets from a computerized precise peristaltic pump that has eight independent channels. During operation, media is drawn from the media reservoir, pumped through the compartments, merged at the outlets of the chambers and returned back to the media reservoir. Using the seeding loop, cells are seeded in each chamber at a flow rate of about 0.1 mL/min as described previously. After the seeding, the main circulating loop is switched on as soon as the inoculation loop is closed. For cryopreservation, a media flask containing cryopreservation fluid can be placed connected to seeding loop. After flushing the HCG constructs with PBS, the cryopreservation fluid can be perfused through the constructs transversely to improve distribution in the scaffolds.

hMSC Seeding in the HCG Scaffolds in Perfusion Bioreactor.

Porous HCG scaffolds can be prepared by solid-liquid phase separation and subsequent sublimation of the solvent following a method published previously. Three (1 mm thick) sterilized HCG scaffolds were stacked in the perfusion chamber as described in our prior publications (52, 13). Cell seeding can be performed following the method detailed in our prior publications (48) and (52). Cell suspension concentration varied by sample and contained between $2 \times 10^5$ and $1 \times 10^6$ cells suspended in 15 mL of media. Seeding is generally completed in about 3 hours. After seeding, complete culture media, such as αMEM with 10% FBS, can be added to the media container and continuously circulated at a speed of about 0.01 mL/min for up to a month with periodic media changes. The individual perfusion chambers can be removed from the system for cellular assays at pre-determined time points. It is noted that the modular design of the perfusion system allow the removal of individual chamber without interrupting system operation.

Cryopreservation in the HCG-hMSC Constructs.

While DMSO-based cryopreservants have been extensive used in cryopreservation, trehalose, a non-reducing disaccharide of glucose, is gaining increasing interest in cryopreservation of human stem cells, including hematopoietic stem cells and adipose-derived stem cells. De Rosa et al. have shown that a combination of DMSO and trehalose, has the best preservation outcome for adipose-derived stem cells with greater viability and differentiation potential (53). In the present invention, the following are examples of cryopreservants that can be used: 1% DMSO+9% trehalose+90% FBS, 4% DMSO+6% trehalose+90% FBS, 8% DMSO+2% trehalose+90% FBS, 10% DMSO+90% FBS, 10% glycerol 90% FBS, and 10% ethylene glycol+90% FBS.

After cultivation in the perfusion bioreactor for a sufficient period of time, e.g., 2 and/or 4 weeks, the media can be removed from the system and replaced with a suitable wash buffer, e.g., PBS. Following washing, the constructs are perfused with cryopreservation fluid using transverse flow mode at 0.1 mL/min. The perfusion chambers can be immediately removed from the system and placed in cryo-containing media and stored at about 4° C. for about 1 hr, at about –20° C. for about 2 hrs, and at about –80° C. overnight. The frozen HCG-hMSC constructs can then be removed from the perfusion chambers and placed in liquid nitrogen for 3 or more months. After storage in liquid nitrogen, the constructs can be removed and thawed in a 37° C. water bath. Cells can be tested in in vitro and in vivo assays.

Example 2

Evaluation of the Cell Viability and Properties of the Cryopreserved Constructs In Vitro In SA 2, cell viability and osteogenic differentiation potential of the cryo-preserved HCG-hMSC constructs will be determined using cellular assays established in our laboratory. The frozen constructs will he thawed and placed in growth media. The cell viability will be determined using MTT assays, whereas osteogenic differentiation will be analyzed by measuring the expression of alkaline phosphates and makers for osteoblasts such as osteocalcin and osteopointin by ELISA. The results of these in vitro experiments will determine the effects of cryopreservation on the cellular properties of the HCG-hMSC constructs.

Experiments Cell Proliferation.

Thiazolyl Blue Tetrazolium Bromide (MTT) will be obtained from Sigma and dissolved in media, 0.8 µm filtered and then stored at –20° C. Media will be removed from samples, cell seeded constructs will be washed with sterile PBS followed by the addition of phenol-free MEM with 10% FBS at the same volume as the original culture volume. MTT solution will then be added to each well at 10% of the media volume, and the samples incubated at 37° C. and 5% $CO_2$ for 3 hours. After incubation, the MTT containing media will be removed and replaced with an equal volume of 0.1 N HCl in 100% isopropanol under agitation. Once the formazan is completely dissolved, the supernatant will be read on a microplate reader at 590 nm and quantified against a standard containing a known number of cells.

Osteogenic Differentiation.

Alkaline phosphatase activity of cells in the HCG constructs will be determined as follows. The constructs will be digested in lysing buffer for 30 minutes. Cell lysate (500 µL) will then be added to 1 mL of substrate and alkaline buffer in a dark centrifuge tube. The mixture will be placed in a 37° C. water bath for 15 min after which the reaction is stopped using 1 mL of 0.5 N NaOH in PBS and read at 405 nm using a microplate reader. P-nitrophenol will be used to construct a standard curves, and unseeded constructs used as blanks. Readings were normalized by cell numbers quantified by MTT assay.

Biochemical Assays.

ELISA assays will be performed for the samples from media and the constructs. For the media samples, standard protocol will be followed. For the construct samples, samples will be fixed with 2.5% glutaraldehyde, permeabilized with 0.5% Triton X and blocked with 10% goat serum and 1% bovine serum albumin. Mouse or rabbit primary antibodies and anti-mouse or anti-rabbit alkaline phosphatase (ALP) tagged secondary antibodies Abeam (Cambridge, Mass.) will be used. The construct samples will be extensively washed in blocking buffer after incubation with each antibody to minimize non-specific binding. P-nitrophenol phosphate ALP substrate will be added and the samples incubated at 37° C. for 30 minutes. The reaction will be stopped with the addition of 0.5 M sodium hydroxide. The supernatant will then be analyzed using a microplate reader at 405 nm. Unseeded HCG scaffolds blanks will be used to establish baseline and all data points are an average of 3 replicates.

Histological Preparation and Examination.

The constructs will be removed from the perfusion bioreactor system at various time points. The constructs will be fixed in 10% neutral-buffered formalin solution (pH 7.2), dehydrated in sequentially increasing ethanol solutions to 100 vol % ethanol, immersed in xylene, and embedded in paraffin. The constructs will be cross-sectioned to 5 m thick sections with a sawing microtome. The cut sections will be stained with Mayer's hematoxylin-eosin (H-E) solution for histological observation under a light microscope connected with a camera.

Example 3

Evaluation of the Regeneration Potential of the Cryopreserved Constructs in Animal Model The osteogenic differentiation capacity of the tissue-engineered construct is a key parameter for evaluation of the construct fabrication strategy. We will use animal model to determine the ectopic bone formation capacity of the constructs preserved under various conditions and compare with the freshly fabricated constructs. Bone formation characterized by histological and biochemical examinations by implanting MSC with porous bioceramics subcutaneously in immunodeficient mice have been demonstrated by multiple investigators (54, 55, 56). Repair of experimentally induced small bone defect has also been shown in small animal models (57, 58). In this project, the constructs produced under various conditions will be implanted subcutaneously in nude mice (CD-1 nude, Charles River) to evaluate in vivo bone formation capacity. After 3 and 5 weeks of implantation, the constructs will be extracted and the expression of osteogenic markers will be evaluated by various histological, immunological, and biochemical assays as outlined in the SA1 and SA2.

Experiments: Animal Model.

A total of 70 CD-1 nude mice (Charles River, Wilmington, Mass.) will be used in the animal experiment. The rats will be 8 weeks old and weigh 30 g. The mice will be assigned to one of the two groups: the 5- and 8-week group. Each group will consists of 35 mice; 8 for TEBC-CP-1, 8 for TEBC-CC-1, 8 for TEBC-CP-2, 8 for TEBC-CC-2, and 3 as controls. Two pieces of samples with area of ~0.3 $cm^2$ from each group will be implanted subcutaneously into the 1 site on the right side of the back and 1 counterpart with the same size from the same group into the left side. A total of 3 mice will be used without implantation as control animal group. For each experimental condition at one time point, a total of 16 samples will be distributed in 8 mice, which provides replicate samples for various assays. This number represents the minimal number required statistically to determine the effects of cryopreservation on in vivo performance by power analysis. The retrieved samples will be placed in cold PBS and prepared for immunostaining, histological, or biochemical assays as outlined in SA1 and SA2. All data will be statistically analyzed to express the mean the standard deviation of the mean. One-way ANOVA will be performed to test for the difference among different groups.

TABLE 1

Time schedule for animal study

| Groups | Week 5 | Week 8 |
|---|---|---|
| TEBC-CP-1 | 8 | 8 |
| TEBC-CC-1 | 8 | 8 |
| TEBC-CP-2 | 8 | 8 |
| TEBC-CC-2 | 8 | 8 |
| Control | 3 | 3 |

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. patent application Ser. No. 13/041,688
1. Characterization of patients with high-energy lower extremity trauma. MacKenzie, E J, Bosse, M J and Kellam, J E et al., *J. Orthop Trauma*, Vol. 14. 455-66, 2000.
2. The Musculoskeletal Effects of Smoking. Porter, S E and Hanley, E N. *J. Am. Acad Orthop* Surg, 9-17, 2001.
3. Inhibition of fracture healing. Gaston, M S and Simpson, A H R W. *J Bone Joint Surg*, 12, 1553-1560, 2007.
4. Are smokers a risk group for delayed healing of tibial shaft fractures? Kyrö A, Usenius J P, Aarnio M, Kunnamo I, Avikainen V. *Ann Chir Gynaecol*, 82, 254-262, 1993.
5. Fracture healing and bone repair: an update. Tosounidisa, T, et al. *Trauma*, 145-156, 2009.
6. Adult mesenchymal stem cells for tissue engineering versus regenerative medicine. Caplan, A I. *J of Cellular Physiology*, 341-347, 2007.

7. Why are MSCs therapeutic? New data: new insight. Caplan, A I. 217, *Journal of Pathology*, 217 318-324, 2009.
8. Study of hydroxyapatite osteoinductivity with an osteogenic differentiation of mesenchymal stem cells. Lin, L W, Chow, K L, and Leng, Y. *J Biomed Mater Res*, 89A, 326-335, 2009.
9. Mesenchymal stem cell: cell-based reconstructive therapy in orthopaedics. Caplan, A I. *Tiss. Eng.*, 11, 1198-1211, 2005.
10. In vitro and in vivo evaluation of differentially demineralized cancellous bone scaffolds combined with human bone marrow stromal cells for tissue engineering. Mauney, J R, Jaquiery, C, et al. *Biomaterials*, Vol. 26. 3173-3185.
11. Effects of hydroxyapatite in 3-D chitosan-gelatin polymer network on human mesenchymal stem cell construct development. Zhao, F, Grayson, W L, Ma, T, Bunnell, B, and Lu, W W. *Biomaterials*, 27, 1859-1867, 2006.
12. Microenvironment Formation and Enhancement of hMSC Osteogenesis in Hydroxyapatite-Chitosan-Gelatin Hydrogel. Hunter, K and Ma, T. *Acta Biomaterialia*, 2010. In Review.
13. Perfusion bioreactor system for human mesenchymal stem cell tissue engineering: Dynamic cell seeding and construct development. Zhao, F and Ma, T. *Biotechnology and Bioengineering*, 91, 482-493, 2005.
14. Effects of Shear Stress on 3-D Human Mesenchymal Stem Cell Construct Development in a Perfusion Bioreactor System: Experiments and Hydrodynamic Modeling. Zhao, F, Chella, R and Ma, T. *Biotechnology and Bioengineering*, Vol. 96. 948-953, 2007.
15. Engineering bone: challenges and obstacles. Logeart-Avramoglou, D, Anagnostou, F; Bizios, R; Petite, H. *J. Cell. Mol. Med.*, 9, 72-84. 2005.
16. Global. Economic and Health Benefits of Tobacco Control: Part 2. Wipfli, H and Samet, J M. *Clin Pharmacol Ther*, Vol. 86, 272-280, 2009.
17. Differential effects of nicotine and smoke condensate on bone cell metabolic activity. Gullihorn, L, Karpman, R and Lippiello, L. *Orthop Trauma*, 19, 17-22, 2005.
18. Effects of indomethacin and nicotine on bone produced by distraction osteogenesis in a rabbit model. Shortt N L, Wood M, Noble B, Simpson A H R *Procs AAOS*, 2007.
19. Effect of nicotine on the rate and strength of long bone fracture healing. Raikin S M, Landsman J C, Alexander V A, Froimson M I, Plaxton N A. *Clin Orthop*, 353, 231-237, 1998.
20. Tobacco extract but not nicotine impairs the mechanical strength of fracture healing in rats. Skott, M, et al. *J Orthop Res*, 24, 1472-1479, 2006.
21. Ankle fusion in a high risk population: an assessment of nonunion risk factors. Perlman M H, Thordarson D B. *Foot Ankle Int*, 491-496, 1999.
22. Smoking and hip fracture; a study of 3617 cases. Johnston, P, Gurusamy, K S and Parker, M J. *Injury*, 152-156, 2006.
23. Smoking and the risk of fracture in older men. Olofsson, H, Byberg, L and Mohsen R, et al. *Journal of Bone and Mineral Research*, 20, 1208-1215, 2005.
24. TGF-beta inducible early gene-1 knockout mice display defects in bone strength and microarchitecture. Bensamoun, S F, Hawse, J R and Subramaniam, M, et al. *Bone*, 39, 1244-1251, 2006.
25. Cigarette smoking decreases TGF-b 1 serum concentrations after long bone fracture. Moghaddam, A, et al. *Injury*, In press, 2010.
26. Hypoxia affects mesenchymal stromal cell osteogenic differentiation and angiogenic factor expression. Potier E, et al. *Bone*, 40, 1078-1087, 2007.
27. Hypoxia inhibits the growth, differentiation and bone-forming capacity of rat osteoblasts. Utting, J C, et al. *Experimental Cell Research*, 40, 1693-1702, 2006.
28. Allograft bone: The influence of processing on safety and performance. Boyce T, Edwards J, Scarborough N. *Orthop Clin North Am*, 30, 571-581, 1999.
29. Preparation and characterization of chitosan-gelatin/nanohydroxyapatite composite scaffolds for tissue engineering applications. Peter, M, Ganesh, N and et al. *Carbohydrate Polymers*, 80, 687-694, 2010.
30. Stimulation of osteoblast responses to biomimetic nanocomposites of gelatin-hydroxyapatite for tissue engineering scaffolds. Kim, H W, Kim, H E and Salih, B. *Biomaterials*, 26, 5221-5230, 2005.
31. The effect of pore size on cell adhesion in collagen-GAG scaffolds. O'Brien, F J and et al., *Biomaterials*, 26, 433-441, 2006.
32. Rat bone marrow stromal cell osteogenic differentiation and fibronectin adsorption on chitosan membranes: The effect of the degree of acetylation. Amaral, I F, et al. *Journal of Biomedical Materials Research Part A*, 75, 387-397, 2005.
33. Molecular interactions in collagen and chitosan blends. Sionkowka, A, et al. *Biomaterials*, 25, 795-801, 2004.
34. Hydroxylapatite binds more serum proteins, purified integrins, and osteoblast precursor cells than titanium or steel. Kilpadi, K L, Chang, P L, and Bellis, S L. *J Biomed Mater Res*, 57, 258-267, 2001.
35. Comparative Analysis of Mesenchymal Stem Cells from Bone Marrow, Umbilical Cord Blood, or Adipose Tissue. Kern, Susanne, et al. *Stem Cells*, 24, 1294-1301, 2006.
36. Isolated allogeneic bone marrow-derived mesenchymal cells engraft and stimulate growth in children with osteogenesis imperfecta: implications for cell therapy of bone. Horwitz E M, Gordon P L, Koo W K, et al. *Proc Natl Acad Sci USA*, 99, 8932-8937, 2002.
37. Transplantability and therapeutic effects of bone marrow-derived mesenchymal cells in children with osteogenesis imperfecta. Horwitz E M, Prockop D J, Fitzpatrick L A, et al. *Nat. Med.*, 5, 309-313, 1999.
38. Nonunions and the potential of stem cells in fracture-healing. Tseng S S, Lee M A, Reddi A H. *J Bone Joint Surg Am*, 90, 92-98. 2008,
39. Marrow cell transplantation for infantile hypophosphatasia. Whyte M P, Kurtzberg J, McAlister W H, et al. *J Bone Miner Res*, 18, 624-636, 2003.
40. Autologous bone marrow stromal cells loaded onto porous hydroxyapatite ceramic accelerate bone repair in critical size defects of sheep long bones. Kon, E, Muraglia, A and et al., *J. Biomed. Mater Res*, 49, 328-337, 2000.
41. Repair of large segmental bone defects using bone marrow stromal cells with demineralized bone matrix. Xu, J Z, Hui, Qin et al., *Orthopaedic Surgery*, 1, 34-41, 2009.
42. Tissue-engineered bone regeneration. Petite et al. *Nat. Biotechnol.*, 18, 959-963, 2000.
43. Tissue-engineered bone repair of sheep cranial defects with autologous bone marrow stromal cells. Shang, Q, et al. *J. Craniofac Surg*, 12, 586-593, 2001,
44. HLA expression and immunologic properties of differentiated and undifferentiated mesenchymal stem cells. Le Blanc K, Tammik C, et al. *Exp Hematol*, 31, 890-6, 2003.
45. Mesenchymal stein cells inhibit and stimulate mixed lymphocyte cultures and mitogenic responses independently of the major histocompatibility complex. Le Blanc, K., Tammik, L., Sandberg, B., Haynesworth, S. E., and Ringden, O. Scand. *J Immunol.*, 11-20. 2003,
46. Optimized cryopreservation method for human dental pulp-derived stem cells and their tissues of origin for banking and clinical use. Woods, E J, et al. *Cryobiology*, 59, 150-157, 2009.
47. Technology Assessment Report. Ronda, R. Confidential Technology Assessment Report, 2010.
48. Human Mesenchymal Stem Cells Tissue Development in 3D PET Matrices. Grayson, W L, Ma, T and Bunnell, B. *Biotechnology Progress*, 20, 905-912, 2004.
49. Perfusion Bioreactor Affects the Nuclear Shape and ECM Structure of Human Mesenchymal Stem Cells in 3D Scaffolds. Zhao, F, Grayson, W L and Ma, T. *Journal of Cellular Physiology*, 219, 421-429, 2009.
50. Hypoxia enhances proliferation and tissue formation of human mesenchymal stein cells. Grayson, W L, Zhao, F, Bunnell, B and Ma, T. *Biochemical and Biophysical Research Communications*, 358, 948-953, 2007.
51. Effects of hypoxia on human mesenchymal stem cell expansion and plasticity in 3D constructs. Grayson, W L, Zhao, F, Izadpanah, R, Bunnell, B, Ma, T. *Journal of Cellular Physiology*, 207, 331-339, 2006.
52. Effects of Filtration Seeding on Cell Density, Spatial Distribution, and Proliferation in Nonwoven Fibrous Matrices. Li, Y, Ma, T et al. *Biotech Progress*, 17, 935-944, 2001.
53. A new method for cryopreserving adipose-derived stem cells: An attractive and suitable large-scale and long-term cell banking technology. De Rosa, A, et al. *Tissue Eng Part C*, 15, 659-667, 2009.
54. Fibroblast growth factor-2 supports ex vivo expansion and maintenance of osteogenic precursors from human bone marrow. Martin, I, et al. *Endocrinology*, 138, 4456-62, 1997.
55. Culture expanded canine mesenchymal stem cells possess osteochondrogenic potential in vivo and in vitro. Kadiyala, S, et al. *Cell Transplantation*, 6, 125-134, 1997.
56. Enhanced ectopic bone formation using a combination of plasmid DNA impregnation into 3D scaffold and bioreactor perfssion system. Hosseinkhani, H, Yamamoto, M and Inatsugu, Y. *Biomaterials*, 27, 1387-1398, 2006.
57. Repair of craniotomy defects using bone marrow stormal cells. Krebsbach, P H, Mankani, M H and Satomura, K. *Transplantation*, 66, 1272-1278, 1998.
58. Effect of bone sialoprotein coating of ceramic and synthetic polymer materials on in vitro osteogenic cell differentiation and in vivo bone formation. Schaeren, S, Jaquiery, C et al. *J Biomed Mater Res A*, 92, 1461-1467, 2010.

I claim:

1. A method for cryopreservation of HCG-cell construct, said method comprising providing a porous HCG scaffold in a perfusion bioreactor, wherein said perfusion bioreactor comprises perfusion chambers that contain said HCG scaffold; seeding cells in said HCG scaffold and perfusing cell culture media through said bioreactor to produce said HCG-cell construct; removing said cell culture media and optionally washing said HCG-cell construct with a physiologically acceptable wash solution; perfusing said HCG-cell construct with a cryopreservation fluid using a transverse flow of said cryopreservation fluid through said HCG-cell construct in said bioreactor; removing HCG-cell construct from said bioreactor and freezing said HCG-cell construct in a cryopreservation fluid at increasingly colder temperatures over a period of time; and optionally storing said frozen HCG-cell construct at a suitable cryogenic temperature.

2. The method according to claim 1, wherein said cell is a stem cell.

3. The method according to claim 1, wherein said cell is from an insect, fish, reptile, amphibian, bird, or mammal.

4. The method according to claim 1, wherein said cell is a human mesenchymal stem cell.

5. The method according to claim 1, wherein said physiologically acceptable wash buffer is PBS.

6. The method according to claim 1, wherein said cryopreservation fluid comprises DMSO and trehalose.

7. The method according to claim 1, wherein said freezing step comprises exposing said HCG-cell construct to about 4° C. for about 1 hour, then about −20° C. for about 2 hours, and then about −80° C. for several hours.

8. The method according to claim 1, wherein said porous HCG scaffold is in the three-dimensional shape of a bone or a portion of said bone.

9. The method according to claim 1, wherein said bone is a femur bone, a tibia, a fibula, a humerus, a radius, an ulna, a patella, a cranial bone, a maxillofacial bone, a spinal bone, a scapula, a clavicle, a carpal or metacarpal bone, a tarsal or metatarsal bone, or a pelvic bone, or any other bone in an animal body.

10. The method according to claim 1, wherein said cryopreserved HCG-cell construct is stored in liquid nitrogen.

11. A cryopreserved cell from an HCG-cell construct prepared according to the method of claim 1.

12. A cryopreserved HCG-cell construct prepared according to the method of claim 1.

13. A kit comprising a cryopreserved cell or an HCG-cell construct prepared according to the method of claim 1 and one or more containers.

14. The kit according to claim 13, wherein said kit further comprises instructions or labeling for the use of said kit.

15. The cell according to claim 11, wherein said cell is a human mesenchymal stem cell.

16. The HCG-cell construct according to claim 12, wherein said cell is a human mesenchymal stem cell.

17. The method according to claim 1, wherein said cryopreservation fluid comprises one or more of DMSO, trehalose, glycerol, ethylene glycol, or serum.

* * * * *

UNITED STATES PATENT AND TRADEMARK OFFICE
CERTIFICATE OF CORRECTION

PATENT NO. : 8,367,059 B2  
APPLICATION NO. : 13/184357  
DATED : February 5, 2013  
INVENTOR(S) : Teng Ma Page 1 of 1

It is certified that error appears in the above-identified patent and that said Letters Patent is hereby corrected as shown below:

In the Specifications:

Column 8,
Lines 17-18, "10% glycerol 90% FBS" should read --10% glycerol + 90% FBS--.

Column 9,
Line 18, "Abeam" should read --Abcam--.

Column 11,
Line 11, "hone" should read --bone--.

Column 12,
Line 65, "stein cells" should read --stem cells--.

Column 13,
Line 1, "Sandberg" should read --Sundberg--.
Line 17, "stein cells" should read --stem cells--.

Signed and Sealed this  
Seventh Day of May, 2013

Teresa Stanek Rea  
*Acting Director of the United States Patent and Trademark Office*